United States Patent [19]

Harrick

[11] Patent Number: 4,886,357

[45] Date of Patent: Dec. 12, 1989

[54] INTERNAL REFLECTION ELEMENT WITH INSENSITIVE EDGES

[76] Inventor: Nicolas J. Harrick, Croton Dam Rd., Ossining, N.Y. 10567

[21] Appl. No.: 240,600

[22] Filed: Sep. 6, 1988

[51] Int. Cl.[4] .............................................. G01J 3/42
[52] U.S. Cl. ..................................... 356/300; 356/244
[58] Field of Search ................................ 356/300, 244

[56] References Cited

U.S. PATENT DOCUMENTS 3,999,855  12/1976  Hirschfeld ........................... 356/338
4,746,179   5/1988  Dahne et al. ........................ 356/133

Primary Examiner—Vincent P. McGraw

[57] ABSTRACT

A novel internal reflection element provided with insensitive edges enabling mounting of the internal reflection element with adhesive or seals without spurious spectra arising from underside interaction with the mounting means.

23 Claims, 10 Drawing Sheets

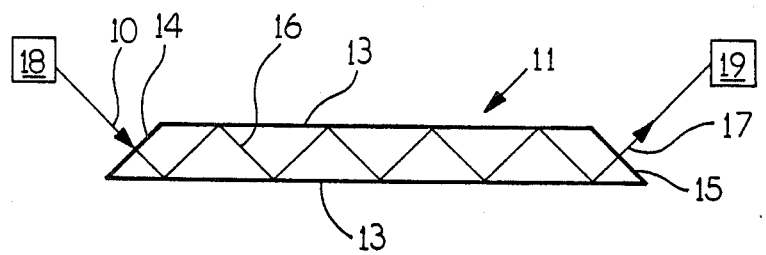
FIG. 1A - PRIOR ART
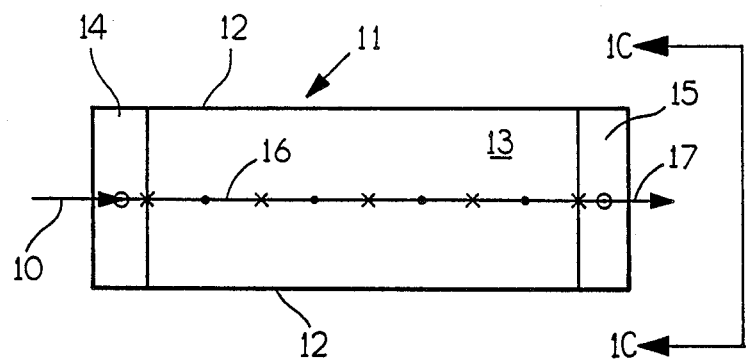
FIG. 1B - PRIOR ART
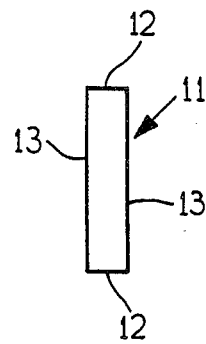
FIG. 1C - PRIOR ART

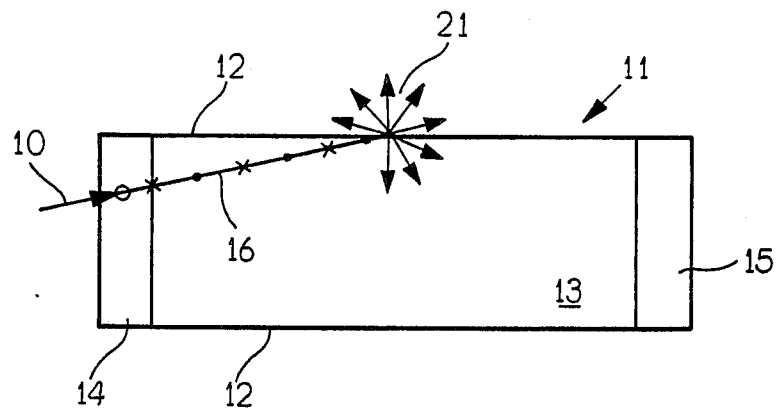
FIG. 2B - PRIOR ART
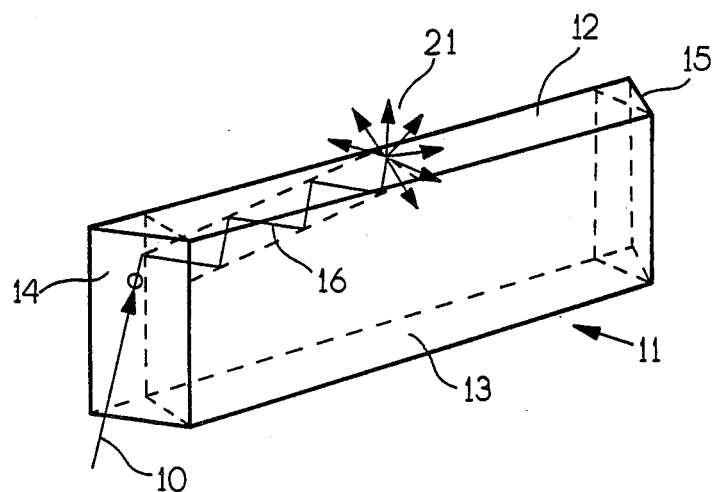
FIG. 2A - PRIOR ART

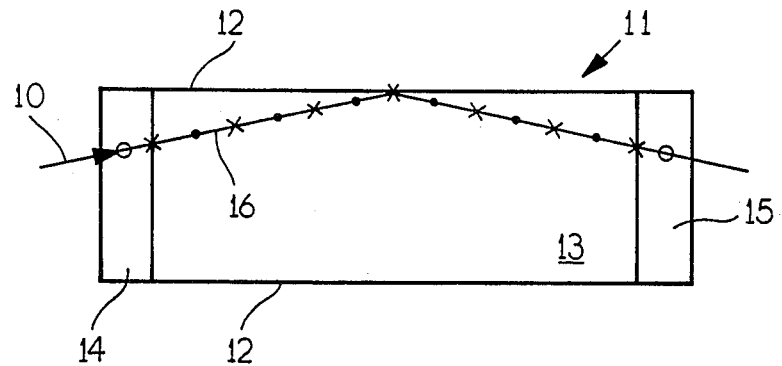
FIG. 3B – PRIOR ART
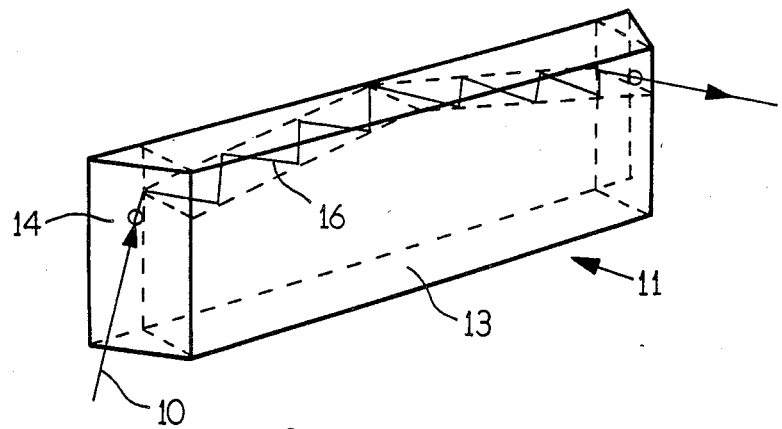
FIG. 3A – PRIOR ART

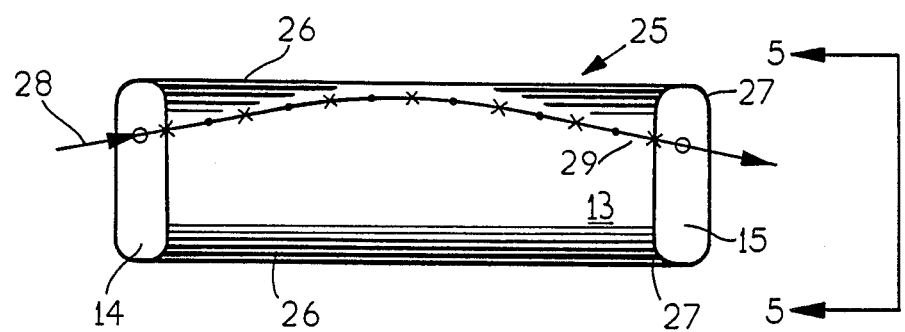
FIG. 4-B
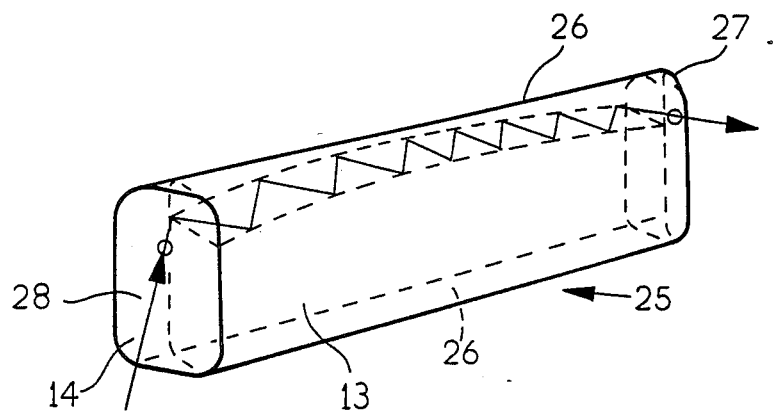
FIG. 4-A

INTERNAL REFLECTION ELEMENT WITH INSENSITIVE EDGES

This invention relates to internal reflection spectroscopy, and in particular to novel internal reflection elements and holders therefor for use in internal reflection spectroscopy apparatus.

BACKGROUND OF INVENTION

Reference is made to my book entitled "Internal Reflection Spectroscopy" published 1967 by Harrick Scientific Corp., Ossining, N.Y., whose contents are incorporated by reference. The book describes the basic techniques of internal reflection spectroscopy (IRS). Chapter IV describes and illustrates various forms of internal reflection elements (IREs) for use in IRS. A typical IRE comprises a flat plate with square side edges and bevelled ends for receiving a beam of radiation (IR, UV, or visible) which propagates down the length of the IRE via multiple internal reflections from the major plane surfaces, the evanescent wave at the reflection points or areas interacting with a sample located on or in contact with a major surface. The resultant interaction modulates the radiation beam which upon exiting from the IRE can be procesed in the spectrometer and upon detection processed electrically to produce a spectrum of radiation beam intensity as a function of beam wavelength which is characteristic of the sample material. Because the radiation within the IRE is usually not collimated, the beam also travels transversely to the long axis of the plate with the result that some of the non-axial or skew rays will strike the IRE edges surfaces, which are typically parallel, plane and orthogonal to the major surfaces. If the edge surfaces are unpolished, a substantial fraction of the radiation is scattered and lost upon reflection from the edges. This results in reduced beam energy or radiation intensity throughput. It is common to polish the edge surfaces to eliminate light scattering by the edge surfaces. But this has the disadvantage that the edge surfaces then become sensitive to materials in contact with them, meaning that the evanescent wave present upon total internal reflection from the polished edge surfaces interact with any material in contact therewith and therefore also contribute to beam modulation. This produces spurious interfering spectra from the IRE holder, O-ring seals, and adhesives used to bond the IRE in its special holder typically along the IRE edge surfaces.

Attempts have been made to eliminate these spurious spectra by placing reflecting metal foils between the IRE edge surfaces and the holder, O-ring seals, adhesives, etc. In other instances, metal reflecting strips, usually of aluminum, have been deposited along the edge surfaces, including the top and bottom, of the IRE. However, the deposition process is a very tedious and expensive process. Moreover, a metallized surface is not a perfect (100%) reflector, and, therefore, energy loss results due to the presence of the metal. For example, the reflectivity of aluminum in air at a wavelength of 2500 cm is 97.5%, while the reflectivity of a zinc selenide (a typical IRE material)-aluminum interface is only 94%. But, after 10 reflections from the ZnSe-Al interface, the energy loss is about 50%, in contrast with the energy loss at total internal reflection from a ZnSe-Air interface which is zero. Hence, as far as is known to me, none of these attempts have proven completely successful, even though the problem has existed for well over 20 years.

BRIEF DESCRIPTION OF THE INVENTION

An object of the invention is to eliminate or at least substantially reduce spurious spectra from an IRE used in IRS.

A further object of the invention is to increase radiation throughput of an IRE.

Still another object of the invention is to eliminate the elaborate and expensive processing of an IRE heretofore used to reduce spurious spectra.

A still further object is novel holders for the IRE especially adapted for analysis of fluid samples.

These and further objects and advantages of the invention as will appear hereinafter are achieved, in accordance with one aspect of the invention, by the remarkably simple expedient of providing non-parallel reflecting surfaces along the long IRE edges. In a preferred embodiment, the edge surfaces are tapered, to produce along the side edges a kind of light funnel. The principle involved is quite simple, and it is surprising that no one has suggested using it before. With a light funnel, as the transverse or skew radiation travels down the funnel along the side edges, the angle of incidence is reduced upon each reflection from the sloping or tapered edge surfaces until eventually the radiation beam reverses its direction of propagation, exits the funnel without reaching the funnel end or tip, and returns to the IRE interior. As a result, the tip of the edge surfaces remains inaccessible to the radiation and thus insensitive to a material in contact with it, and substantially no loss of energy results.

Normally, radiation entering a dielectric (as opposed to a metallic) funnel head-on will eventually escape through the reflecting surfaces because the angle of incidence will eventually reach values less than the critical angle for total internal reflection. But, in the case of an IRE plate as used in IRS spectrometry with tapered long edges in accordance with the invention, the radiation approaches the edges at large grazing angles and so the critical angle is not reached. For example, light propagating down the length of an IRE at an angle of incidence of. 45° and transversely at a skew angle of, say, 3°, strikes the flat reflecting surfaces at an angle of 45.1° and at more than 42° at the sloping long edge surfaces. These angles are well above the critical angle for a typical IRE of ZnSe (with a refractive index of 2.4, the critical angle equals 24.6°). Hence, little if any radiation is lost at the edge surfaces.

Such an IRE with insensitive edge surfaces is not much more difficult to fabricate than the prior art IRE with parallel square side edges. Moreover, it has the additional advantages that there is no need to polish the edge surface portions which are inaccessible to the radiation, nor is there a need to be concerned about contamination of such edges by handling or mounting. In accordance with this respect of the invention, the tapered side edges can be flat or curved. A preferred embodiment has semicylindrically-shaped side edges.

In accordance with another aspect of the invention, prisms in optical contact with the same or opposite major surfaces of the IRE are used in place of the beveled edges as the means for bringing the radiation beam into the IRE and allowing the modulated beam to exit from the IREA. These entrance and exit means have the advantage that they can be located spaced inward from the short side edges of the plate. Thus, the plate portions from these means to the short side edges also become insensitive as no radiation is present therein and thus can conveniently be used as support means for the IRE on its holder. This feature allows the use of a holder for liquid or paste samples wherein the IRE becomes the base element of the holder and supported on the latter solely along insensitive edge portions avoiding the undesirable spurous spectra.

In accordance with a modification of the latter aspect of the invention, the IRE plate is configured as a circular disc with the entrance and exit means united to form a ring or doughnut configuration in optical contact with a major surface of the disc. The opposite major surface for receiving a liquid or paste specimen constitutes the bottom of a cylindrical holder sealed to the IRE disc by an O-ring contacting the IRE at an insensitive edge portion.

DESCRIPTION OF DRAWINGS

The invention will now be described in greater detail, reference being had to the accompanying drawings wherein:

FIGS. 1a, 1b and 1c are, respectively, side, top and end views of a typical known IRE with square edges, also illustrating an ideal radiation path;

FIGS. 2a and 2b are, respectively, perspective and top views of the IRE of FIG. 1 showing light scattering from unpolished side edges;

FIGS. 3a and 3b are views similar to FIGS. 2a and 2b showing the effect of polishing the side edges.

FIGS. 4a and 4b are, respectively, perspective and top views of one form of IRE in accordance with the invention;

FIG. 5a is a view through the center of the actual IRE.

FIG. 6 is a view similar to FIG. 5 of a modification and FIG. 6a is a view similar to FIG. 5a;

DETAILED DESCRIPTION OF PREFERRED EMBODIMENTS

Figure 5B:
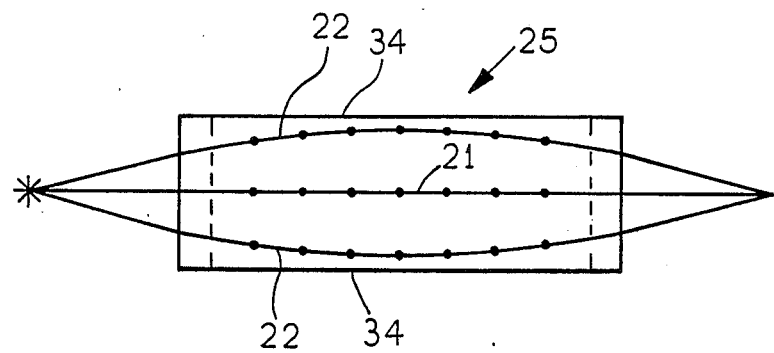
FIG. 5b illustrates the beam paths in a view similar to FIG. 3c.

FIGS. 1-3 illustrate the problem in connection with a typical known IRE, as described for example on pages 100-103 of my published book. In IRS, the spectrometer generates a beam of desired radiation 10, typically UV, IR or visible, whose wavelength can be varied. The beam is directed into a sample chamber where the IRE, designated 11, is mounted on a suitable support; for a single-pass, flat plate IRE, typically along its long side edges 12. The sample to be analyzed is placed in contact with one or both major plate surfaces 13. A bevelled end 14 is provided on the plate 11 to allow incident beam radiation 10 to impinge upon a major surface 13 at an angle exceeding the critical angle, and thus the beam propagates as shown at 16 down the length of the plate and exits the plate at the opposite bevelled end 15. The exiting beam 17 is redirected back into the spectrometer, detected, and the resultant electrical signal processed in the normal way to produce, typically on a strip chart recorder, a spectrum of beam intensity as a function of wavelength. Since this is all well-known in the art, the apparatus described has been schematically illustrated by a radiation source 18 and a detector 19.

In the real world, the beam 16 doesn't actually follow the ideal path illustrated in FIG. 1 because it is not perfectly collimated. Actually, some of the radiation inevitably is directed transversely, referred to as skew radiation, and will ultimately come in contact with the long side edges 12. If the latter are unpolished, then total internal reflection is frustrated and some radiation will scatter, thus exiting the IRE at the side edges. This has been illustrated at 21 for one skew ray 16 in FIG. 2. Incidentally, in the top views in the various figures in the drawings, the dots along the rays indicate reflections at the top major surface, and the crosses represent ray reflections at the bottom major surface. The scatter is indicated by numeral 21. If the edge surfaces 12 are polished to avoid scatter by total internal reflection of the skew ray, the result is illustrated in FIG. 3. No scatter results, but now the problem arises as described above that the polished side edge surfaces 12 become active or sensitive, and thus any material in contact therewith interacts with the evanescent wave at a totally reflecting surface causing modulation of the beam and thus spurious spectra in the output. The various schemes known to avoid this problem as described in the introduction have not proven completely satisfactory, because of the complex and elaborate processing needed, and the energy losses resulting.

The novel concept underlying this aspect of the invention is to provide structure or means along the long side edges of the IRE, typically used to support same within the spectrometer, which will ensure total internal reflection of any skew rays while leaving inaccessible to the radiation portions or regions of the side edges which thus do not become involved in the total internal reflection of the skew rays. In a preferred embodiment of the invention, the long side edges are providd with a funnel type structure which will cause skew rays to be totally internally reflected back into the IRE interior as illustrated in FIG. 3, while assuring that the tip or end of the funnel remains inaccessible to the skew ray and thus uninvolved in redirecting the skew rays without energy loss back into the IRE interior. Thus, the funnel tip remains insensitive, and can be used to mount or support the IRE within the spectrometer.

One embodiment in accordance with this aspect of the invention provides a curved side edge configuration, preferably semi-cylindrical. This is illustrated in FIG. 4. The IRE, designated 25 is otherwise identical to that illustrated in FIG. 4 and the same reference numerals are used for those elements, except that the side edges may be tapered, with curved or flat sides. Both configurations can be broadly described as funnel-like, and the principle of operation will be illustrated in the greatly enlarged cross-sectional or end schematic views illustrated in FIGS. 5 and 6.

Figure 6:
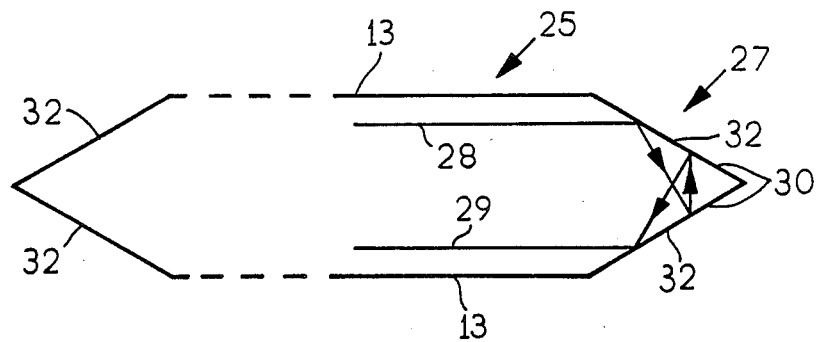
Figure 5:
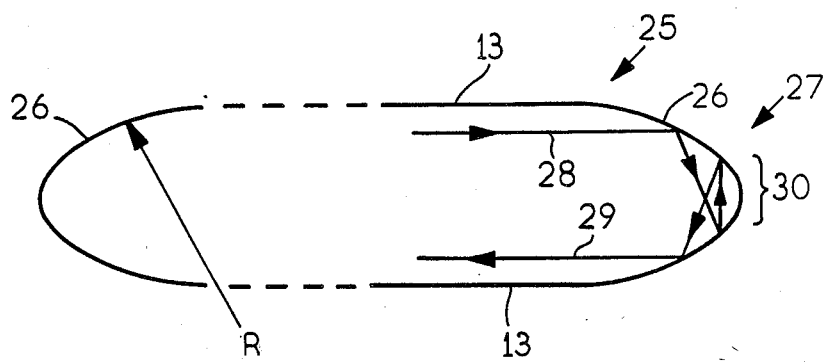
FIG. 5 is a greatly-elongated schematic end view illustrating the principles of operation of the IRE of FIG. 4.
Figures 5A, 6A:
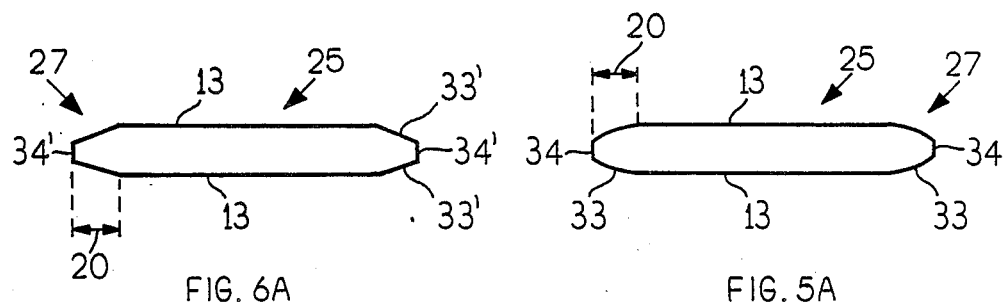

When a skew ray designated 28 reaches the side edge 26 and enters the funnel indicated generally by 27, it will multiply reflect at increasing angles of incidence as shown and ultimately becomes redirected 29 back into the IRE interior. The significant point is that the funnel tip, indicated by reference 30, cannot be reached by the skew rays 28. Since no total internal reflection takes place at the funnel tip 30, no evanescent wave exists there and therefore no interaction with the radiation beam 28, 29 is possible. Thus, materials may be placed in contact with that tip region 30 without fear of contamination of the surface and creating spurious spectra. It is understood that FIGS. 5 and 6 are intended to illustrate the principles underlying this aspect of the invention, and that in reaity the radiation is travelling down the longitudinal direction of the IRE plate and not transversely as depicted in FIGS. 5 and 6. In a typical situation, the skew angle is about 3° off of the long axis of a plate whose dimensions typically are about 10 mm wide, about 1 mm thick, and about 50 mm long. Since the tips along the long side edges are not reached by the radiation, they can be truncated or removed. FIGS. 5a and 6a more accurately depict the cross-section of an IRE in accordance with the invention. In FIG. 5a, the IRE plate 25 has rounded long side edges 33 truncated to a flat surface 34. In FIG. 6a, the long side edges are tapered 33′ again terminating at flat surfaces 34′. The flat surfaces which in this embodiment extend perpendicular to the major surfaces 13 are never reached by the radiation propagated down the plate.

The geometry of the funnel 27 to achieve this desired result can be readily calculated knowing the critical angle and the funnel length required. In general, for a curved funnel having a length of about 1 mm, the dimension indicated by 20 in FIG. 5a, the radius of curvature, indicated by R in FIG. 5, should range from about 75 to 300 mm. With this geometry, the radiation will penetrate about ½ mm into the funnel before being redirected back toward the center. The curved shape needn't be semi-cylindrical; /moreover the insensitive tip portion 30 can be extended to provide a longer surface area for supporting the IRE. This is illustrated, for example, in FIG. 6, though the semi-cylindrical shape of FIG. 5 is easier to fabricate. In the modification of FIG. 6, flat sides 32 can be tapered to form the funnel-like shape as illustrated. Preferably, the included angle between the flat sides 32 should vary between about 3° and 5°. Again, as illustrated in FIG. 6a, the edges can be truncated at 34′ since the radiation will only penetrate about half the distance indicated by numeral 20. Thus, the outer half remains insensitive and can be used to support the plate on its holder, such as by a suitable epoxy adhesive.

An example of a useful geometry will assist those skilled in the art in selecting the appropriate funnel configuration. For example, for a ZnSe IRE with IR radiation, the radius of curvature R for the FIG. 5a embodiment should be about 150 mm, and for the flat tapered embodiment of FIG. 6a, the included angle should be about 4°.

Figure 3C:
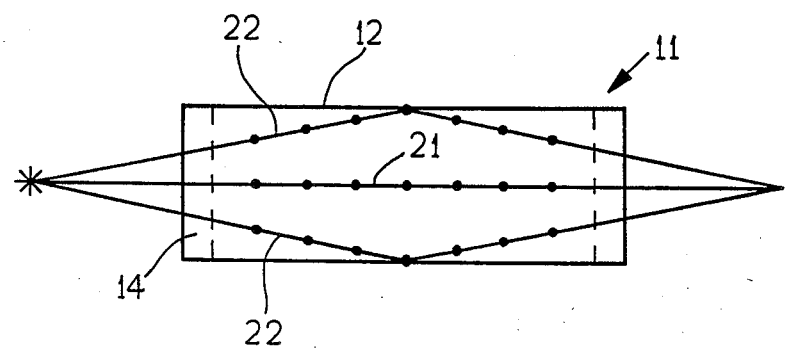
FIG. 3c is a top view showing some beam paths.

FIGS. 3c and 5b schematically illustrate the effects. FIG. 3c shows in a plan view of the prior art IRE element depicted in FIGS. 3a and 3b the path of radiation through the long direction of the plate for a center axial ray 21 and two skew rays 22. Note that the skew rays 22 reach the side edges 12. In the corresponding view of the IRE of the invention depicted in FIG. 5b, under the same conditions, the skew rays 22 do not reach the side edge 34 and thus the latter remain insensitive.

Figure 7A:
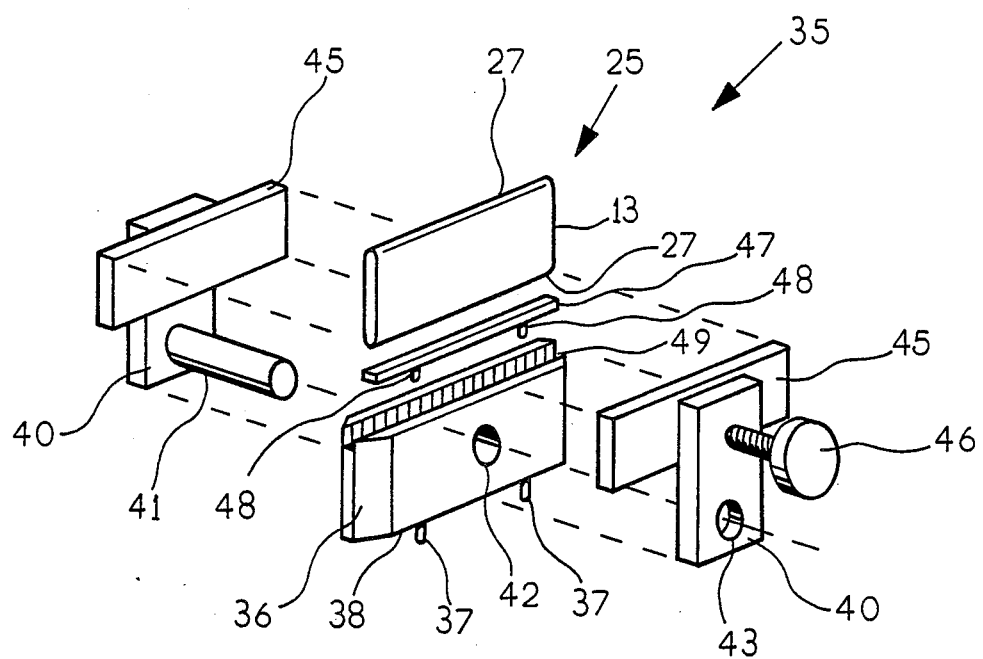
FIGS. 7a and 7b are, respectively, exploded and perspective views of a novel holder for the IRE of the invention.

Since the tip regions 30 of the long side edges does not receive any radiation, it need not be polished. Only the portions of the funnel surfaces from which total internal reflection is desired need be polished. Since the tip region therefore remains insensitive, the IRE can be supported at said tip region 30 without fear of contamination or spurious spectra generation. One such holder taking advantage of this novel feature of the invention is illustrated in FIG. 7. The holder, designated 35, comprises an elongated base member 36, generally plate-like, which has at its lower long edge 38 pins 37 which are adapted to engage corresponding holes in the support surface of the sampling chamber of the spectrometer. The pins 37 are used to locate the assembly in the sampling chamber. Two end vertical members 40 are positioned and mounted on opposite sides of the base 36 and by means of a pin 41 on one engaging holes 42 in the base and 43 in the opposite vertical member, serve to support the vertical members 40 on the base 36. Two pressure plates 45 are mounted on respective vertical members 40. A knurled thumb screw 46 engages one vertical member 40 and the free hidden end bears against one of the pressure plates 45. The assembly so-far described forms a simple C-clamp.

The IRE 25 is mounted as by any suitable adhesive to a mounting plate 47 along the insensitive region 30 extending along one of its long side edges 27 with the funnel configuration. The plate 47, provided with locating pins 48, seats inside a slot 49 extending along the top of the base 36. Holes (not shown) at the bottom of the slot 49 receive the pins 48 and thus serve to locate the IRE 25 accurately on the holder. It will be appreciated that the locating means described are used to locate the IRE in the sampling chamber so as to receive the incident beam, redirected usually by mirrors within the sampling chamber, at the correct angle at its entrance face, the bevelled end 14. The C-clamp is not used to hold the IRE 25 in position. it is merely used to allow a sample to be prssed tightly against the major surfaces of the IRE. Usually, the tighter the contact, the higher the signal-to-noise level up until intimate contact is achieved. Thus, the sample, not shown, would be placed to cover the full area of the major surfaces 12, 13 and extend completely between the latter and the facing flat surfaces of the pressure plates 45. The larger the sampling area in the length direction, again the larger the signal-to-noise ratio. Also, the presence of the sample prevents the pressure plates 45 from contacting the active surface of the IRE and thus produce spurious spectra.

Figure 7B:
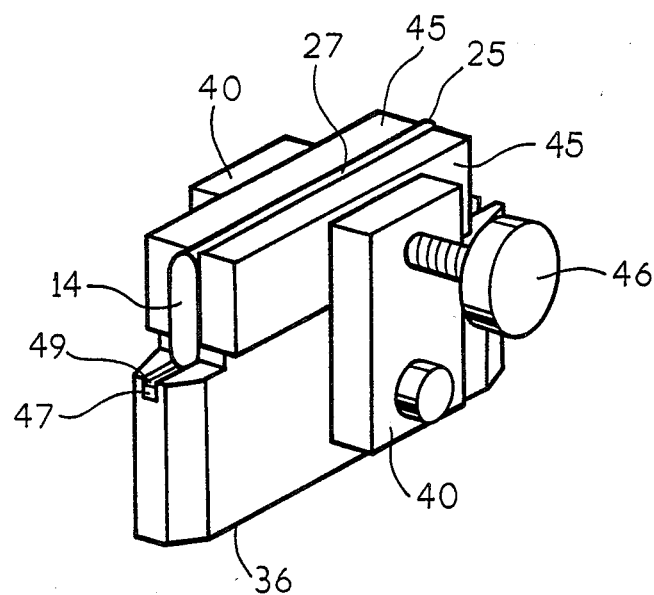

As will be observed from FIG. 7b, the portions of the plate polished major surfaces opposite the beveled entrance 14 and exit 15 end surfaces does receive radiation. If those plate portions were to be provided with an adhesive for sealing purposes, to avoid detecting the adhesive, it is desirable to metallize those regions before applying the adhesive. This burdensome and expensive.

Figure 8:
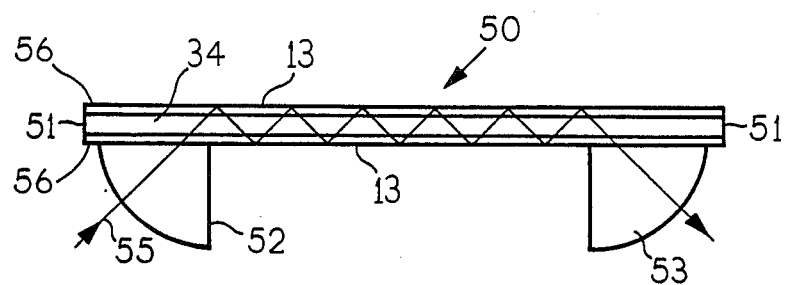
FIG. 8 is a side view of another embodiment of an IRE in accordance with the invention.

FIG. 8 shows an embodiment in accordance with the invention which avoids the above noted problem. The IRE element shown and referenced 50 is the same as depicted in FIGS. 4a and 4b except that the short edges 51 are no longer beveled, but are square. Now, the entrance and exit means are provided by prisms 52 and 53, respectively, called quarter rounds in my book, in optical contact with the bottom major surface 13 of the plate. However, the prisms are inset from the ends. The incident radiation 55 enters on the curved prism side, passes into the plate, propagates down to the end and exits in a similar fashion from the prism 53. Location of the prisms prevents the plate ends indicated by 56 from receiving radiation. Thus the plate short ends remain insensitive and can be used to help support the IRE element, in addition to the funnel long side edges 34.

Figure 9:
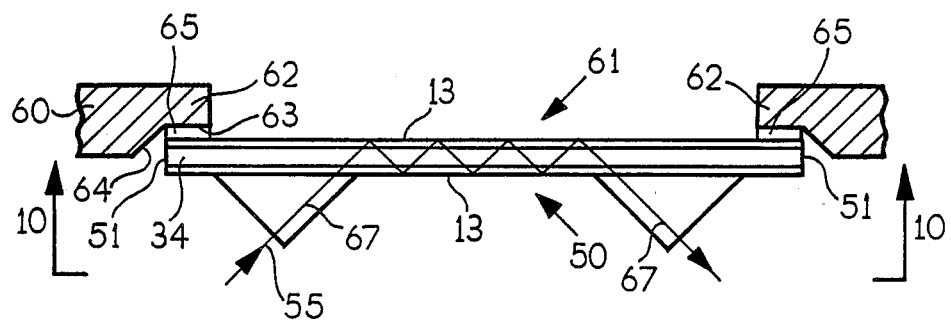
FIGS. 9 and 10 are side cross-sectional and bottom views, respectively, of an IRE mounted on a holder for analyzing fluid samples in accordance with the invention.
Figure 10:
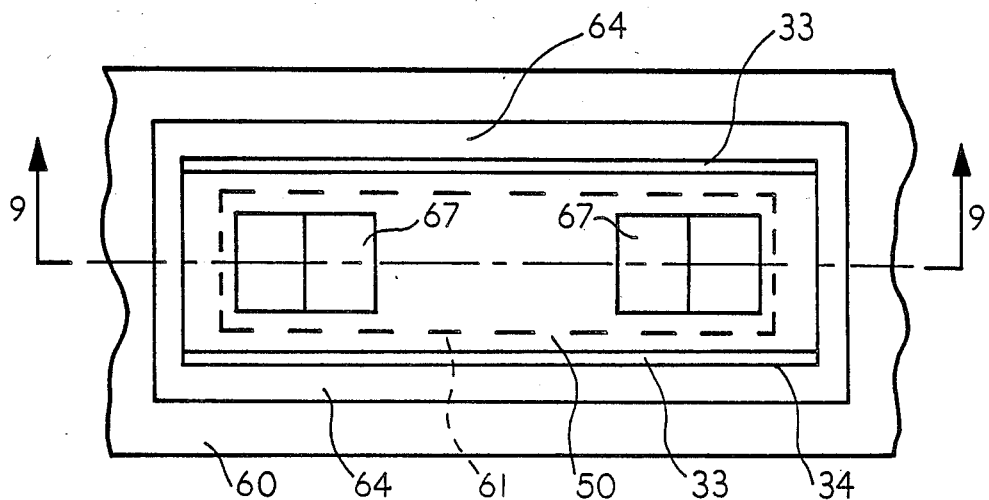

This combination of features is used to good advantage in a novel IRE and holder for use with liquid or paste samples, illustrated in FIGS. 9 and 10. A large support plate 60 of any suitable nmaterial, preferably non-corrosive metal, has a rectangular opening 61. As shown in the cross-sectional view of FIG. 9, the opening 61 comprises a first rectangular opening 62 forming a lateral annular shelf 63 which bevels outward at 64. An IRE 50 as depicted in FIG. 8 is mounted on the annular shelf 63 as by a suitable epoxy adhesive 65. Along the long side edges of the IRE, the shelf 63 is narrower to ensure that the adhesive only contacts the insensitive regions of the long side edges. The shelf 63 can be wider at the ends, because prisms are used as the entrance and exiting means for the radiation. The prisms can be the quarter rounds depicted in FIG. 8, or triangular shaped as shown in FIG. 9 at 67. The latter would be fixed angle, single-pass multiple internal reflection plates, whereas those employed in the FIG. 8 embodiment would be variable-angle, single-pass plates. Due to the radiation paths taken, the short edge regions of the plate remain insensitive, as well as the funnelled long side edges. This allows the IRE plate to seal off the opening 61, since adhesive can now extend completely round the entire IRE plate periphery, without fear of spurious spectra due to the intimate contact of the adhesive to the IRE surfaces. Thus, the IRE can now act as a support for a liquid or paste sample that can be dropped or placed into the cavity formed by opening 61 and remain in contact with the major IRE surface 13 and bounded by the opening walls 62. Bringing in and removing the radiation from the bottom simplifies the analysis of liquid samples. While similar constructions have been attempted in the past, metallization was necessary where the IRE mounted to the plate holder. The embodiment depicted in FIGS. 9 and 10 requires no metallization, since all contact between the IRE plate and the holder occurs only along insensitive regions of the IRE plate.

Figure 11:
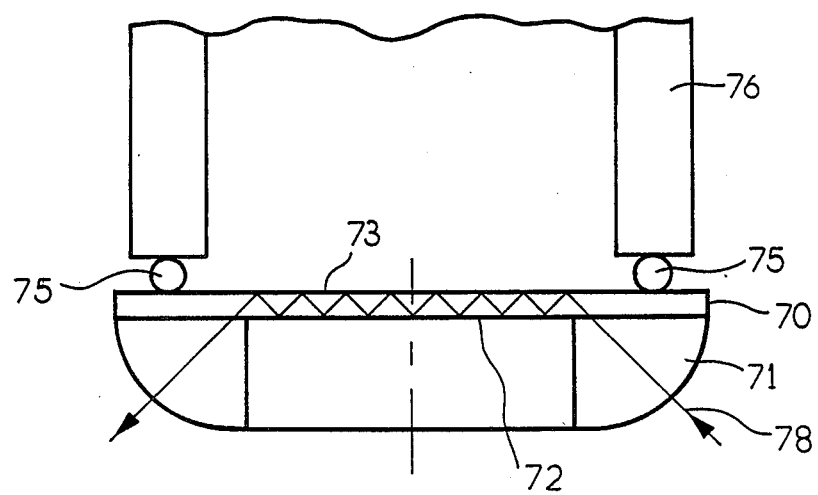
FIGS. 11 and 12 are side and bottom views, respectively, of a modification for analyzing fluid samples.
Figure 12:
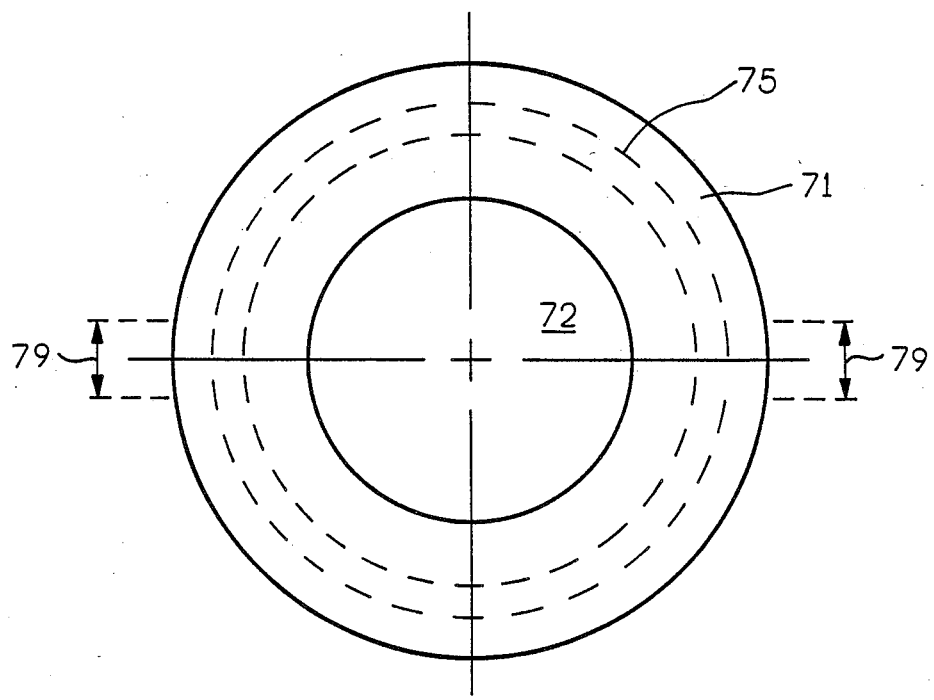

FIGS. 11 and 12 depict a variation also suitable for conducting analyses of liquid or paste samples. In this embodiment, the IRE 70 is a circuoar plate or disc, instead of rectangular as in the other embodiments. Entrance and exit means for a beam of radiation is provided by an annular quarter round prism 71 optically contacted to the bottom major surface 72 of the IRE disc 70. The top major surface 73 receives the sample to be analyzed. The sample surface 73 is sealed off by an O-ring 75 arranged between the sample surface 73 and an upright cylinder 76. Means, not shown, can be provided to urge the cylinder 76 against the O-ring 75 to maintain the sample area sealed off. As shown, the radiation beam 78, having a typical width as shown at 79 in FIG. 12, enters the quarter round 71 and then the IRE disc, propagates across the disc and exits at the opposite side. For a typical 50 mm diameter disc, the beam width would be about 10 mm. The configuration is such that the radiation beam stays clear of the peripheral disc regions contacted by the O-ring 75. Thus, no spurious spectra due to the O-ring are present. The construction shown has the advantage that the assembly can be rotated about a vertical axis, thus causing the beam to access different diagonal regions of the sample, which may be desirable for certain samples. Another advantage is that the doughnut shaped prism automatically ensures alignment of the entrance and exit prism parts, whereas in the FIG. 10 embodiment, the two prisms 67 would have to be carefully aligned.

While the invention has been described in connection with a single pass, multiple reflecting IRE plate, it will be appreciated that the principles described herein can be employed with double-pass plates, as well as with other IRE configurations at the edge surfaces where the IRE is to be supported within the sampling chamber and thus it is desirable to provide an insensitive region thereat. Thus, in connection with the embodiments of FIGS. 5 and 6, if used in a holder as illustrated in FIG. 7, only one long edge needs to have the funnel configuration, namely, the edge adhered to the mounting plate 47. The opposite long edge at the top, being uncontacted, need not have the funnel shape except that the IRE is easier to handle if opposite long edges have insensitive regions, since the user need not fear contaminating such insensitive regions while cleaning or mounting of the IRE in its holder.

In addition, it will be clear that other holders providing for mounting or supporting of the IRE along an insensitive region are also within the teachings of my invention as will be evident to those skilled in this art.

My invention offers a number of important benefits, which are here summarized:

1. There is no need to polish the side edge regions that will remain insensitive, no need there be any fear of contamination of those side edges by handling or mounting. Thus, if desired, the IRE of the invention can be embedded into a metal plate with shielding, as, for example, by metal strips, required only in the vicinity of the bevel entrance and exit faces.

2. By allowing pins to be bonded to the IRE edge, the IRE can be reproducibly mounted in both the longitudinal and transverse directions in a holder in the sampling chamber and leave the sampling surfaces, i.e., the major plate surfaces, totally exposed for maximum sensitivity. Also, the bonded support pins is a sturdy arrangement which holds the IRE fixed and hence maintains optical alignment when solid samples are applied to the sampling surfaces. Moreover, the pinned IRE allows simplification of the IRE holder. The pressure plates are relatively free to move and thus exert little or no strain on the IRE crystal.

3. The invention is applicable to the most popular IRE configurations, namely, single and double pass, multiple reflection plates, as well as other IRE geometries.

4. The use of curved side edges eliminates sharp corners thus avoiding chipping of the IRE edges.

5. The area of the insensitive regions can be controlled by adjusting the curvature and width of the sloping surfaces near the edges. The geometry of the funnels is generally independent of the plate thickness and length. Thus, the IRE can be positioned to receive the incident radiation at a desired, well-defined angle of incidence. This produces superior spectra. Plate thickness, for example, can vary between 0.25-2 mm, and plate lengths typically from 5-10 cm.

6. No energy losses are experienced since total reflection is employed to redirect the skew rays back into the IRE interior.

7. The IRE can be composed of the wide range of materials indicated in my book, for use with IR, UV or visible radiation.

8. The benefits of the invention can be achieved with narrow plates that are less costly to fabricate.

9. Moreover, analysis of fluid specimens becomes very simple requiring minimum preparation effort by the user.

Other modifications will be within the skill of the art and are intended to be within the scope of my invention.

What is claimed is:

1. A internal reflection element for use in internal reflection spectroscopy, comprising:
   a radiation-transparent body having at least one sampling surface and an entrance surface for receiving a beam of radiation at an angle causing the beam to propagate through the body by reflection from the sampling surface at an angle exceeding the critical angle, said body having at least one surface whereby it can be supported,
   and means along said supporting surface for preventing exiting of any radiation incident thereon and without modulating said radiation.

2. An internal reflection element as set forth in claim 1 wherein said preventing means comprises said supporting surface being configured to form a generally funnel-shape such that radiation entering the funnel-shaped surface reflects off of the funnel surfaces at increasing angles of incidence exceeding the critical angle causing such radiation to be redirected back into the interior of the body.

3. A internal reflection element for use in internal reflection spectroscopy, comprising:
   a radiation-transparent body having at least one sampling surface and an entrance surface for receiving a beam of radiation at an angle causing the beam to propagate through the body by reflection from the sampling surface at an angle exceeding the critical angle,
   said body having at least one edge surface whereby it can be contacted for supporting same,
   and means along said supporting edge surface for causing total reflection of any radiation incident thereon while leaving a region of said edge surface insensitive to materials present thereon.

4. An internal reflection element for use in internal reflection spectroscopy, comprising:
   an elongated radiation-transparent body having major sampling surfaces and at one end an entrance surface for receiving a beam of radiation at an angle causing the beam to propagate down the body by multiple reflections from the major surfaces at angles exceeding the critical angle, said body having long side edge surfaces extending generally parallel to the direction of the beam propagation down the body,
   and funnelling means along the side edge surfaces to cause any radiation incident thereon by total reflection to be redirected back into the body interior, said funnelling means being configured to prevent a region thereof from receiving any such radiation thereby rendering said region insensitive to any contacting materials.

5. An internal reflection element as set forth in claim 4 wherein said long side edge surfaces are configured to form a generally truncated funnel-shape such that radiation entering the funnel-shaped side edges reflects off of the funnel surfaces at increasing angles of incidence exceeding the critical angle causing such radiation to be redirected back into the interior of the body.

6. An internal reflection element as set forth in claim 4 wherein said element comprises an elongated flat plate with a bevel at a short end for receiving or transmitting said radiation beam, each of the long side edges of the plate from opposite plate sides being tapered.

7. An internal reflection element as set forth in claim 4 wherein said element comprises an elongated flat plate with a bevel at a short end for receiving or transmitting said radiation beam, each of the long side edges of the plate being rounded to form a truncated semi-cylindrical shape.

8. An internal reflection element as set forth in claim 6 wherein the angle formed between the tapered sides is in the range of about 3–5 degrees.

9. An internal reflection element as set forth in claim 7 wherein the radius of the semi-cylinder is in the range of about 75–300 mm.

10. An internal reflection element as set forth in claim 4 and further comprising means for supporting said element along the insensitive region of the long side edges where radiation cannot be incident.

11. An internal reflection element as set forth in claim 4 wherein said insensitive regions are unpolished.

12. An internal reflection element as set forth in claim 4 and further comprising means including locating means bonded to the insensitive region of the funnelling means.

13. An internal reflection element as set forth in claim 12 wherein the locating means comprise outwardly projecting pins.

14. In internal reflection spectroscopy, an internal reflection element comprising a radiation-transparent body having at least one sampling surface and an entrance surface for receiving a beam of radiation at an angle causing the beam to propagate through the body by reflection from the sampling surface at an angle exceeding the critical angle, said body having peripheral edge surfaces whereby it can be contacted and supported, means for contacting said body at its peripheral surfaces, and means for rendering said contacted peripheral edge surfaces insensitive to the beam propagating through the body.

15. The element of claim 14 wherein the means comprise prism entrance and exit members in optical contact with a major surface of the body.

16. The element of claim 15 wherein the body is disc-shaped, and the prism means is ring shaped.

17. A holder in combination with a multiple pass IRE plate and comprising a base member, means on the base for reproducibly locating a receiving area for said IRE, said IRE having an insensitive edge surface, means associated with said insensitive edge surface and adapted to mate with the base receiving area for reproducibly locating the IRE on the base member.

18. The combination as set forth in claim 17 wherein the means associated with the insensitive edge surface comprises pins, and the base receiving area comprises holes for receiving the pins.

19. The combination as set forth in claim 17 and further comprising clamping means mounted on the base for pressing a sample material against major surfaces of the IRE.

20. A holder in combination with a multiple pass IRE plate for analyzing fluid samples, comprising an IRE plate having major surfaces, long side edges and short side edges, means rendering said long side edges insensitive, means sealing the insensitive long side edges and the short side edges to an opening in the holder, and means for bringing radiation into and removing radiation from the plate, said last-named means preventing the radiation from reaching the short side edges of the plate.

21. The combination of claim 20 wherein the sealing means is an adhesive, and the radiation bringing and removing means comprises prisms optically contacting a major surface of the plate.

22. In internal reflection spectroscopy, in combination, a multiple-reflection IRE plate for analyzing fluid samples and comprising a generally disc-shaped plate having major surfaces, a ring-shaped prism in optical contact with a major surface of the plate, means sealing the periphery of the plate at its opposite major surface, said sealing means being located relative to the prism such that radiation entering the plate via the prism remains spaced from the sealing means, means for directing radiation into the plate via the prism, and means for detecting the radiation exiting from the plate via the prism, the major surfaces of the plate inside the ring-shaped prism being free of contact with materials other than the fluid sample to be analyzed.

23. The combination of claim 22 for analyzing fluid samples wherein a cylinder is provided, and the sealing means is an O-ring located between the cylinder and the plate, the fluid sample being provided on the opposite major surface within the cylinder.

* * * * *